US011236064B2

(12) United States Patent
Sánchez Casals et al.

(10) Patent No.: US 11,236,064 B2
(45) Date of Patent: Feb. 1, 2022

(54) METHOD FOR PREPARING 3-[(3S)-7-BROMO-2-OXO-5-(PYRIDIN-2-YL)-2,3-DIHYDRO-1H-[1,4]-BENZODIAZEPIN-3-YL] PROPIONIC ACID METHYL ESTER, AND COMPOUNDS USEFUL IN THAT METHOD

(71) Applicant: Moehs Iberica S.L., Rubí-Barcelona (ES)

(72) Inventors: Carles Sánchez Casals, Rubí-Barcelona (ES); Alicia Dobarro Rodríguez, Rubí-Barcelona (ES)

(73) Assignee: MOEHS IBERICA S.L., Barcelona (ES)

( * ) Notice: Subject to any disclaimer, the term of this patent is extended or adjusted under 35 U.S.C. 154(b) by 0 days.

(21) Appl. No.: 16/634,448

(22) PCT Filed: Jul. 27, 2018

(86) PCT No.: PCT/EP2018/070414
§ 371 (c)(1),
(2) Date: Jan. 27, 2020

(87) PCT Pub. No.: WO2019/020790
PCT Pub. Date: Jan. 31, 2019

(65) Prior Publication Data
US 2021/0139452 A1   May 13, 2021

(30) Foreign Application Priority Data
Jul. 28, 2017  (ES) ............... ES201730986

(51) Int. Cl.
*C07D 401/04* (2006.01)
*C07D 213/50* (2006.01)
*C07D 487/04* (2006.01)

(52) U.S. Cl.
CPC ......... *C07D 401/04* (2013.01); *C07D 213/50* (2013.01); *C07D 487/04* (2013.01)

(58) Field of Classification Search
CPC . C07D 401/04; C07D 213/50; C07D 487/042
See application file for complete search history.

(56) References Cited

U.S. PATENT DOCUMENTS

2019/0359619 A1* 11/2019 Ben-Zion ............. C07D 401/04
2020/0239477 A1*  7/2020 Sanchez Casals ... C07D 487/04

FOREIGN PATENT DOCUMENTS

| CN | 108 264 499 A | 7/2018 |
| WO | WO 00/69836 A1 | 11/2000 |
| WO | WO 2011/032692 A1 | 3/2011 |

OTHER PUBLICATIONS

Butini; Bioorg. Med. Chem. Lett. 23 (2013) 85-89. (Year: 2013).*
Greene, Theodora W., et al., "Chapter 7: Protection for the Amino Group" *Protective groups in organic synthesis*. Wiley, 1999, pp. 494-653.
Gustavo A. Escobar Grupos protectores 2015 (http://aprendeenlinea.udea.edu.co/lms/moodle/pluginfile.php/90435/mod_resource/content/0/Archivos_del_curso/CAPITULO_4._GRUPOS_PROTECTORES.pdf).
International Search Report issued in International Application PCT/EP2018/070414 dated Oct. 24, 2018.
International Preliminary Report on Patentability issued in International Application PCT/EP2018/070414 dated Jul. 11, 2019.
Leganza A. et al., European Journal of Organic Chemistry, 2006, 13, 2987-2990.
Written Opinion of the International Searching Authority issued in International Application PCT/EP2018/070414 dated Oct. 24, 2018.

* cited by examiner

*Primary Examiner* — Daniel R Carcanague
(74) *Attorney, Agent, or Firm* — Knobbe, Martens, Olson & Bear, LLP

(57) ABSTRACT

The present disclosure relates to a method for preparing 3-[(3S)-7-bromo-2-oxo-5-(pyridin-2-yl)-2,3-dihydro-1H-[1,4]-benzodiazepin-3-yl] propionic acid methyl ester from (2-amino-5-bromo-phenyl)-pyridin-2-yl-methanone. Also disclosed are compounds useful as intermediates in the method, methyl (4S)-4-amino-5-[4-bromo-2-(pyridin-2-carbonyl)anilino]-5-oxo-pentanoate hydrobromide salt and methyl (4S)-4-(benzyloxycarbonylamino)-5-[4-bromo-2-(pyridin-2-carbonyl)anilino]-5-oxo-pentanoate.

5 Claims, 5 Drawing Sheets

METHOD FOR PREPARING 3-[(3S)-7-BROMO-2-OXO-5-(PYRIDIN-2-YL)-2,3-DIHYDRO-1H-[1,4]-BENZODIAZEPIN-3-YL] PROPIONIC ACID METHYL ESTER, AND COMPOUNDS USEFUL IN THAT METHOD

CROSS-REFERENCED TO RELATED APPLICATIONS

This application is the U.S. National Phase under 35 U.S.C. § 371 of International Application No. PCT/EP2018/070414, filed Jul. 27, 2018, designating the U.S., and published in English as WO 2019/020790 A1 on Jan. 31, 2019, which claims priority to Spanish Patent Application No. P201730986, filed Jul. 28, 2017, the entire contents of which are incorporated herein by reference.

INVENTION

The present invention relates to a method for preparing 3-3S)-7-bromo-2-oxo-5-(pyridin-2-yl)-2,3-dihydro-1H-[1,4]-benzodiazepin-3-yl] propionic acid methyl ester from (2-amino-5-bromo-phenyl)-pyridin-2-yl-methanone, and new compounds useful as intermediates in that method.

BACKGROUND

International application WO 00/69836 describes short-acting [1,4]-benzodiazepines which include a carboxylic ester moiety and are inactivated by non-specific tissue esterases. An organ-independent elimination mechanism is predicted to be characteristics of these benzodiazepines, providing a more predictable and reproducible pharmacodynamic profile. The compounds are suitable for therapeutic purposes, including sedative-hypnotic, anxiolytic, muscle relaxant and anticonvulsant purposes. The compounds are short-acting CNS depressants that are useful to be administered intravenously in the following clinical settings: preoperative sedation or ICU sedation, anxiolysis, and amnestic use for perioperative events; conscious sedation during short diagnostic, operative, or endoscopic procedures; as a component for the induction and maintenance of general anesthesia, prior and/or concomitant to the administration of other anesthetic or analgesic agents.

Example Ic-8 of document WO 00/69836 describes a general method for preparing benzodiazepine derivatives, such as 3-[(4S)-8-bromo-1-methyl-6-(pyridin-2-yl)-4H-imidazo[1,2-a][1,4]benzodiazepin-4-yl]-propionic acid methyl ester of formula (F) from the lactam of formula (D).

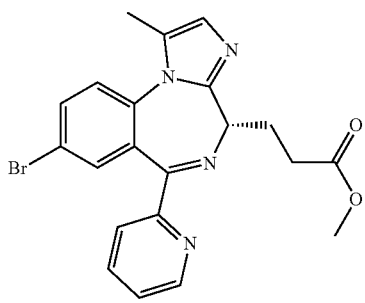

(F)

In turn, it also describes the method of preparing lactam (D) from precursor (A). Said method consists of reacting (2-amino-5-bromo-phenyl)-pyridin-2-yl-methanone of formula (A) with (2S)-2-(fluorenyl-9-methoxycarbonylamino)-5-methoxy-5-oxo-pentanoic acid chloride, giving rise to the amide of formula (B1).

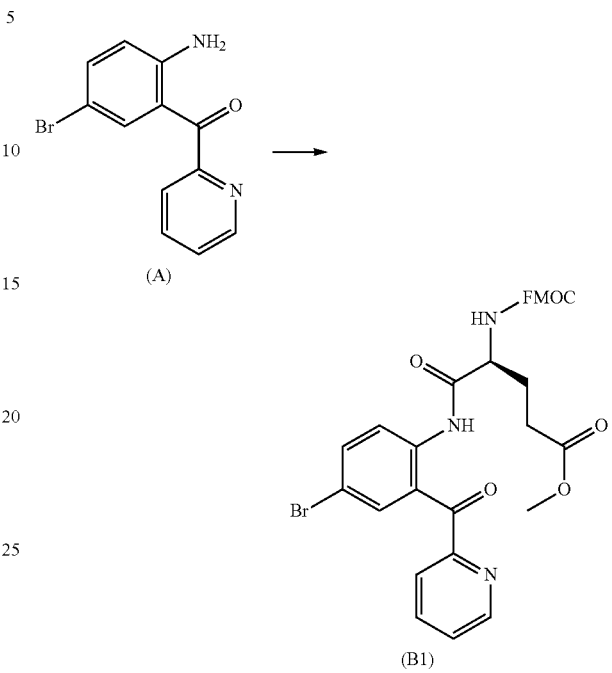

The document teaches that the treatment of B1 with triethylamine in dichloromethane followed by treatment with acetic acid in dichloromethane gives rise to the lactam, 3-[(3S)-7-bromo-2-oxo-5-(pyridin-2-yl)-2,3-dihydro-1H-[1,4]-benzodiazepin-3-yl]propionic acid methyl ester of formula (D).

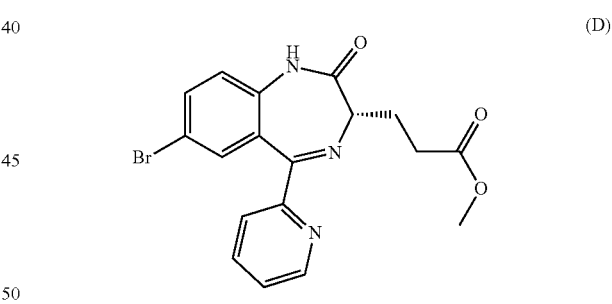

The method of obtaining (F) according to WO 00/69836 consists of reacting the compound of formula (D) with a suspension of NaH in THF, treating the reaction mixture with bis-morpholinophosphorylhydrochloride (BPMC) in THF, filtering the reaction mixture, reacting the filtrate with DL-1-amino-2-propanol, purifying the alcohol adduct that is obtained, treating that purified alcohol adduct with a mixture of DMSO and oxalyl chloride in dichloromethane, treating the reaction mixture with triethylamine, diluting with ethyl acetate, washing with aqueous solutions, and concentrating to give a foam, treating that foam with a catalytic amount of p-toluenesulfonic acid, neutralizing the solution with sodium bicarbonate, and isolating the compound of formula (F).

However, the method comprises a large number of steps, leading to insufficient optical purity of the compounds obtained in the different steps and a low overall yield. For these reasons, the method of WO 00/69836 is not satisfactory for production at the industrial level.

International application WO 2011/032692 also describes the method for synthesizing [1,4]-benzodiazepine of formula (F) and the benzenesulfonic acid salt thereof from the lactam of formula (D).

In this case, the synthesis pathway of the lactam of formula (D) also starts with (2-amino-5-bromo-phenyl)-pyridin-2-yl-methanone of formula (A) but (A) is reacted with tBoc (tert-butyloxycarbonyl)-protected glutamate, giving rise to methyl (4S)-4-(tert-butyloxycarbonylamino)-5-[4-bromo-2-(pyridin-2-carbonyl)anilino]-5-oxo-pentanoate of formula (B). The deprotection of the amide of formula (B) is performed by means of treatment with HCl, giving rise to the methyl (4S)-4-amino-5-[4-bromo-2-(pyridin-2-carbonyl)anilino]-5-oxo-pentanoate hydrochloride salt of formula (C).

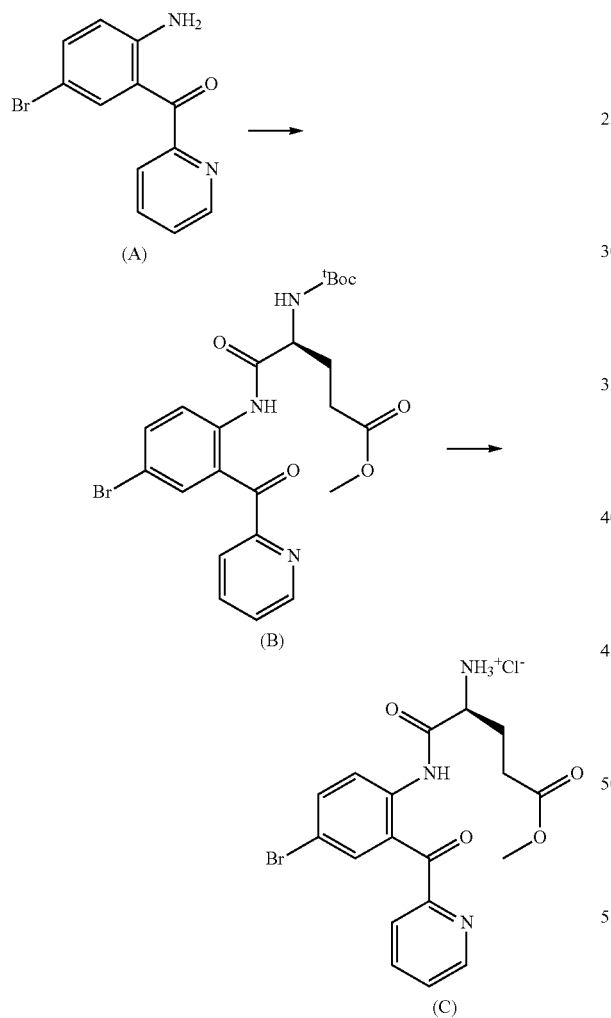

In WO 2011/032692, the treatment of (C) with a base gives rise to the cyclized compound of formula (D), i.e., the lactam 3-[(3S)-7-bromo-2-oxo-5-(pyridin-2-yl)-2,3-dihydro-1H-[1,4]-benzodiazepin-3-yl] propionic acid methyl ester. The lactam of formula (D) is reacted with lithium diisopropylamide (LDA) and bis-morpholinophosphorylchloride (BMPC) to give rise to 3-[(3S)-7-bromo-2-(bis-morpholinophosphoryloxy)-5-(pyridin-2-yl)-3H-[1,4]-benzodiazepin-3-yl]-propionic acid methyl ester of formula (E1). The latter is reacted with (R)-1-amino-2-propanol or (S)-1-amino-2-propanol in an aprotic solvent to give rise to 3-[(S)-7-bromo-2-((R and/or S)-2-hydroxy-propylamino)-5-(pyridin-2-yl)-3H-[1,4]-benzodiazepin-3-yl]-propionic acid methyl ester of formula (EM).

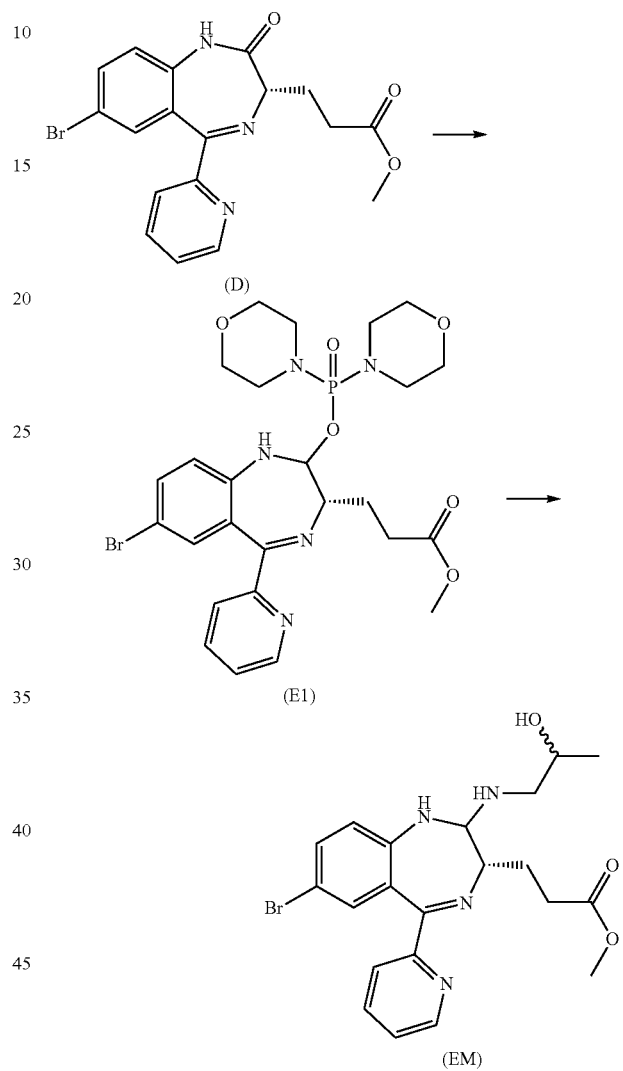

To obtain 3-[(4S)-8-bromo-1-methyl-6-(pyridin-2-yl)-4H-imidazo[1,2-a][1,4]benzodiazepin-4-yl]-propionic acid methyl ester of formula (F), document WO 2011/032692 describes reacting the compound of formula (EM) with an oxidizing agent in an acidic medium.

SUMMARY

The authors of the present invention have developed a new method for synthesizing the intermediate of formula (D) with significantly higher reaction yields and providing products having a higher purity than the methods described in the state of the art.

Therefore, a first aspect of the invention relates to a method for preparing 3-[(3S)-7-bromo-2-oxo-5-(pyridin-2-yl)-2,3-dihydro-1H-[1,4]-benzodiazepin-3-yl] propionic acid methyl ester of formula (D)

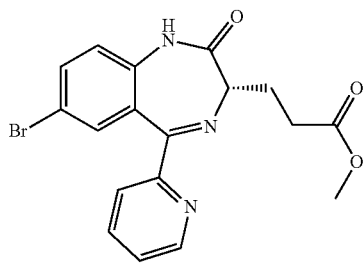
(D)

characterized in that it comprises the step of reacting methyl (4S)-4-amino-5-[4-bromo-2-(pyridin-2-carbonyl)anilino]-5-oxo-pentanoate hydrobromide salt of formula (I-C)

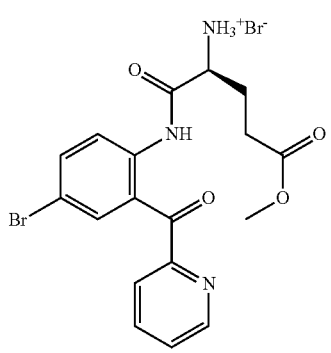
(I-C)

with a base.

In a second aspect, the invention relates to a method for preparing 3-[(4S)-8-bromo-1-methyl-6-(pyridin-2-yl)-4H-imidazo[1,2-a][1,4]benzodiazepin-4-yl]-propionic acid methyl ester of formula (F)

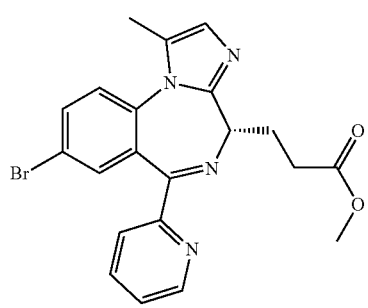
(F)

characterized in that it comprises the steps of:
a) reacting the compound of formula (D)

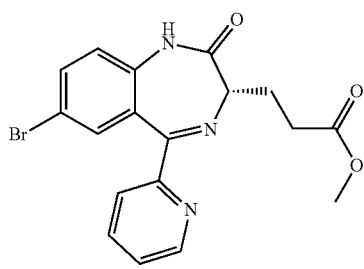
(D)

obtained by means of the method of the first aspect of the invention with lithium diisopropylamide (LDA) and bis-morpholinophosphorylchloride (BMPC) to obtain the compound of formula (E1)

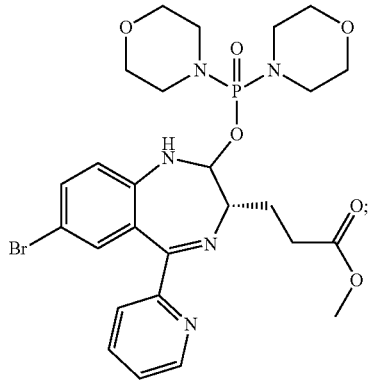
(E1)

b) reacting the compound of formula (E1) obtained in step (a) with (R)-1-amino-2-propanol or (S)-1-amino-2-propanol to obtain the compound of formula (EM)

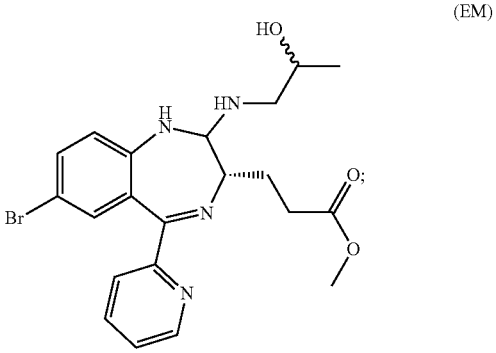 [SMILES: COC(=O)CC[C@@H]1N=C(c2ccccn2)c2cc(Br)ccc2NC1NCC(C)O]
(EM)

and
c) reacting the compound of formula (EM) obtained in step (b) with the Dess-Martin periodinane oxidizing agent.

In a third aspect, the present invention relates to the use of methyl (4S)-4-amino-5-[4-bromo-2-(pyridin-2-carbonyl)anilino]-5-oxo-pentanoate hydrobromide salt of formula (I-C)

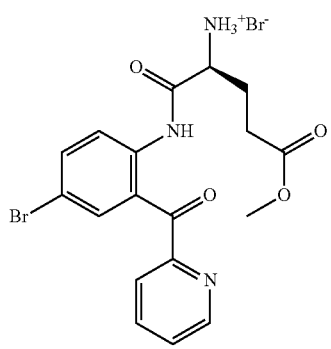
(I-C)

for preparing a compound of formula (F)

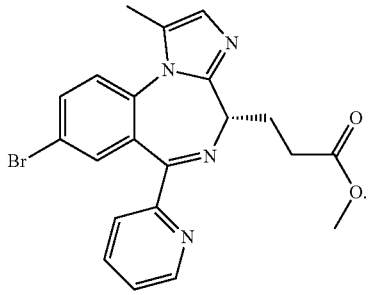
(F)

In a fourth aspect, the present invention relates to the use of methyl (4S)-4-(benzyloxycarbonylamino)-5-[4-bromo-2-(pyridin-2-carbonyl)anilino]-5-oxo-pentanoate of formula (I-B)

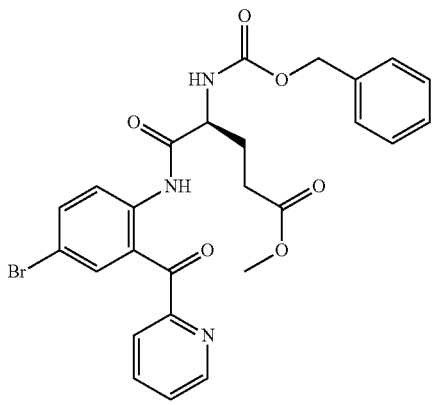
(I-B)

and methyl (4S)-4-amino-5-[4-bromo-2-(pyridin-2-carbonyl)anilino]-5-oxo-pentanoate hydrobromide salt of formula (I-C)

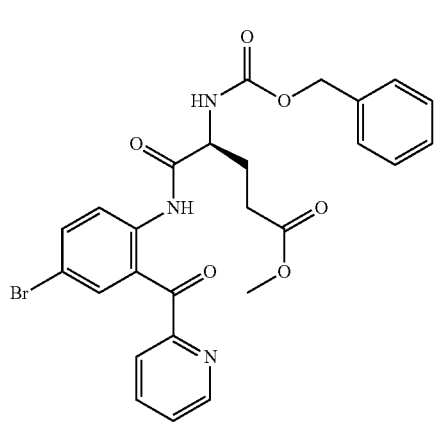
(I-B)

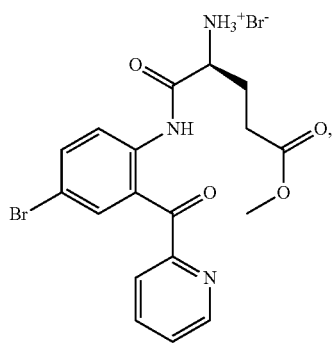
(I-C)

respectively.

Figure 1:
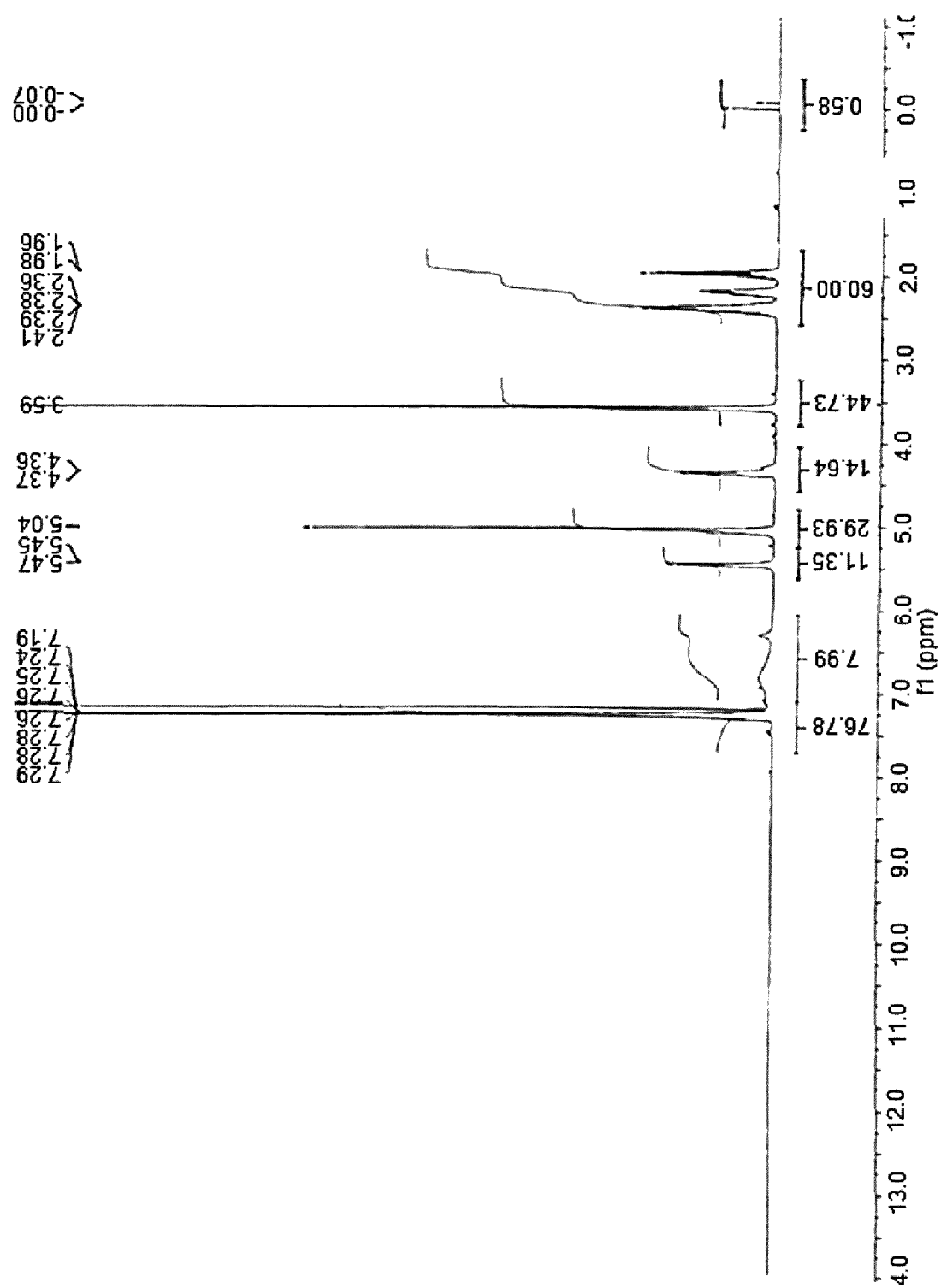
FIG. 1 shows the 1H-NMR of (2S)-2-(benzyloxycarbonylamino)-5-methoxy-5-oxo-pentanoic acid.

for preparing a compound of formula (F)

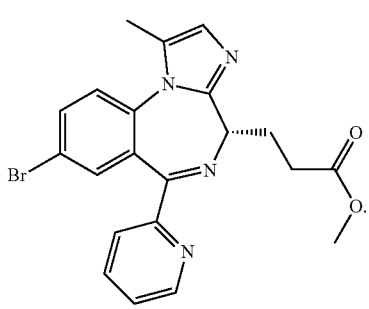
(F)

The fifth and sixth aspects of the present invention relate to the compounds methyl (4S)-4-(benzyloxycarbonylamino)-5-[4-bromo-2-(pyridin-2-carbonyl)anilino]-5-oxo-pentanoate of formula (I-B)

DETAILED DESCRIPTION

The first aspect of the invention relates to a method for preparing 3-[(3S)-7-bromo-2-oxo-5-(pyridin-2-yl)-2,3-dihydro-1H-[1,4]-benzodiazepin-3-yl] propionic acid methyl ester of formula (D)

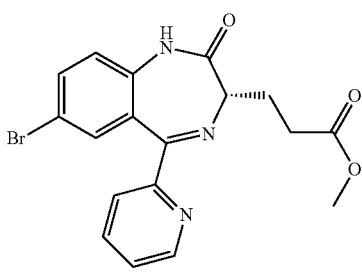

(D)

characterized in that it comprises the step of reacting methyl (4S)-4-amino-5-[4-bromo-2-(pyridin-2-carbonyl)anilino]-5-oxo-pentanoate hydrobromide salt of formula (I-C)

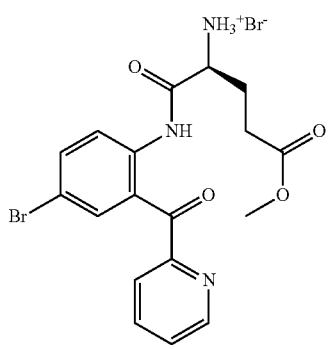

(I-C)

with a base.

Throughout this specification and the attached claims, the term "base" is used to describe any substance capable of accepting protons, increasing the pH of a solution. In an aqueous medium, said substance supplies said medium with $OH^-$ ions. The strength of a base can be measured through the pKb constant, where the stronger the base is the lower its pKb will be.

Therefore, in the first aspect of the invention the compound of formula (I-C) is converted into the compound of formula (D) in the presence of a base. In a preferred embodiment of the invention, the base used for converting the compound (I-C) into the compound (D) is a base with a pKb of less than 8.0. Non-limiting suitable examples of bases that may be used are alkali hydroxides such as NaOH or KOH, carbonic acid salts such as sodium bicarbonate or potassium bicarbonate, or also non-nucleophilic amines such as triethylamine ($Et_3N$) or N,N-diisopropylethylamine (DIPEA). The base used is preferably sodium bicarbonate.

Generally, the reaction for forming the compound of formula (D) from the compound of formula (I-C) can be carried out in an aqueous medium with a pH value comprised between 3 and 8, preferably between 3 and 5, more preferably between 3.5 and 4.5, even more preferably with a pH value comprised between 3.8 and 4.

In a particular embodiment, the solvents in which the reaction for converting (I-C) into (D) can be carried out are selected from water and alcohols, preferably form water, methanol, ethanol, propanol, isopropanol, and butanol, and more preferably water.

In another particular embodiment, the reaction for converting (I-C) into (D) is carried out at a temperature comprised between 0° C. and 40° C., preferably between 20° C. and 30° C., and more preferably between 20 and 23° C.

In another particular embodiment, the reaction for converting (I-C) into (D) is carried out using water as a solvent and at a temperature comprised between 20 and 30° C.

Generally, the reaction for converting (I-C) into (D) is carried out by means of an acid-base equilibrium, so it occurs almost immediately. Therefore, in a particular embodiment the reaction for converting (I-C) into (D) is initiated by subjecting the compound of formula (I-C) to the pH values described above, and it is considered that the reaction ends in less than 1 hour, preferably in less than 30 minutes, more preferably in less than 15 minutes, even more preferably in less than 5 minutes.

The compound of formula (D) is soluble in at least alkyl esters, toluene, methyltetrahydrofuran, and dichloromethane. Therefore, in a particular embodiment, after reaching the pH values described above by means of adding a base to an acidic aqueous solution of the compound of formula (I-C), for example, the compound of formula (D) can be isolated by adding dichloromethane to said acidic aqueous solution (liquid-liquid extraction). The evaporation of dichloromethane produces the compound of formula (D) in solid state.

In a particular embodiment, the solid of the compound of formula (D) obtained according to the preceding paragraph can be purified by means of recrystallization, preferably by means of recrystallization using a solvent in which the compound (D) has a high solubility, preferably a solubility not lower than 1 g/L, and adding an antisolvent, i.e., a solvent in which the compound (D) has a low solubility, preferably a solubility not higher than or equal to 1 g/L. Preferred solvents include, among others, ketones and alcohols, preferably acetone and isopropanol. Preferably, the compound of formula (D) is dissolved in isopropanol and the latter is heated at reflux temperature. Preferred antisolvents include water, alkanes and ethers, preferably n-heptane or methyl tert-butylether. Preferably, water or n-heptane are selected as the antisolvent for recrystallizing the compound of formula (D). In general, the purity of the compound of formula (D) can be determined by means of nuclear magnetic resonance (NMR) or by means of liquid chromatography.

In a preferred embodiment, the compound of formula (I-C) is prepared by means of reacting methyl (4S)-4-(benzyloxycarbonylamino)-5-[4-bromo-2-(pyridin-2-carbonyl)anilino]-5-oxo-pentanoate of formula (I-B)

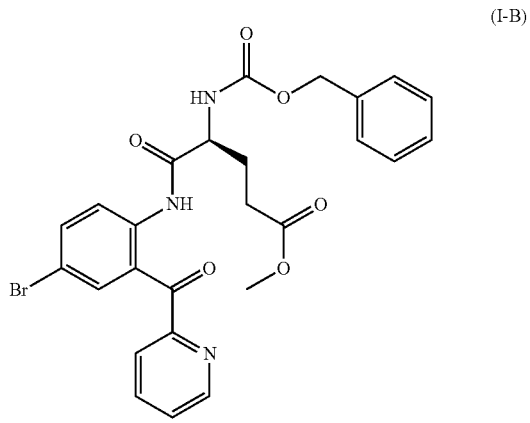 [SMILES: COC(=O)CC[C@H](NC(=O)OCc1ccccc1)C(=O)Nc1ccc(Br)cc1C(=O)c1ccccn1]

(I-B)

with hydrobromic acid.

The intermediate of formula (I-B) can be dissolved in glacial acetic acid at a low temperature, such as, for example, between 10 and 20° C., preferably between 10 and 12° C. Hydrobromic acid (HBr) can be added to this acidic solution to achieve amine deprotection by means of the CBz group leaving and to thereby obtain the compound of formula (I-C).

In a particular embodiment, the intermediate of formula (I-B) can be dissolved in acetic acid, dichloromethane, toluene, or methyl tert-butylether, preferably in glacial acetic acid. In another particular embodiment, the intermediate of formula (I-B) can be dissolved in any of the solvents mentioned at a temperature of 10° C. to 20° C., preferably 10° C. to 12° C.

In a particular embodiment, the reaction for forming the compound of formula (I-C) from the compound of formula (I-B) is carried out by means of slowly adding HBr dissolved in glacial acetic acid to a solution of (I-B) previously dissolved in acetic acid as described above, at a temperature comprised between 10 and 20° C. Once the addition of HBr has ended, in a particular embodiment the temperature is left to go up to between 15 and 25° C., preferably to 20° C. In a particular embodiment, the resulting acidic solution is left stirring for 1 to 3 hours, preferably for 2 hours.

In a particular embodiment, the compound of formula (I-C) thereby formed is not isolated and the resulting acidic medium is directly neutralized until reaching the aforementioned pH values. In a particular embodiment, said resulting acidic medium can be neutralized by means of adding sodium bicarbonate to the acidic aqueous solution of the compound of formula (I-C). Said neutralization is the neutralization of the aforementioned acidic medium, giving rise to the reaction for converting the compound of formula (I-C) into the compound of formula (D).

Alternatively, the compound of formula (I-C) can be isolated by treating the corresponding reaction mass with a suitable organic solvent, preferably an alkyl acetate, more preferably isopropyl acetate, to obtain a solid which is filtered.

In another preferred embodiment, methyl (4S)-4-(benzyloxycarbonylamino)-5-[4-bromo-2-(pyridin-2-carbonyl)anilino]-5-oxo-pentanoate of formula (I-B) is prepared by means of reacting the compound of formula (A)

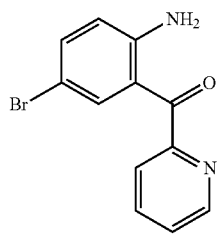
(A)

with (2S)-2-(benzyloxycarbonylamino)-5-methoxy-5-oxo-pentanoic acid in the presence of a coupling agent. The compound (2-amino-5-bromo-phenyl)-pyridin-2-yl-methanone of formula (A) is known in the state of the art, its preparation is described, for example, in the publication by Leganza A. et al., *European Journal of Organic Chemistry*, 2006, 13, 2987-2990, and it can also be identified according to its CAS number: 1563-56-0.

(2S)-2-(benzyloxycarbonylamino)-5-methoxy-5-oxo-pentanoic acid can be represented according to the following structural formula

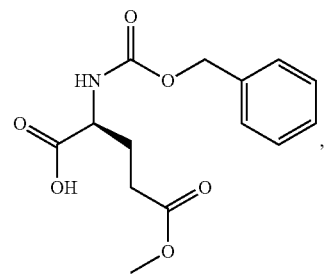 [SMILES: COC(=O)CC[C@H](NC(=O)OCc1ccccc1)C(=O)O]

and can be obtained by means of the method described in Example 1, protecting (2S)-2-amino-5-methoxy-5-oxo-pentanoic acid with benzyl chloroformate.

One skilled in the art will recognize the meaning of coupling agent which, in the present context, refers to an amino-acid coupling agent. An example of coupling agent capable of facilitating the formation of amide groups by means of reaction between an $NH_2$ group and a COOH group is N,N'-diisopropylcarbodiimide (DCI) or N,N'-dicyclohexylcarbodiimide (DCC).

In a preferred embodiment, the coupling reaction between the compound of formula (A) and (2S)-2-(benzyloxycarbonylamino)-5-methoxy-5-oxo-pentanoic acid is carried out in dichloromethane in the presence of a coupling agent. In another preferred embodiment, the coupling reaction between the compound of formula (A) and (2S)-2-(benzyloxycarbonylamino)-5-methoxy-5-oxo-pentanoic acid is carried out in dichloromethane in the presence of a coupling agent and at a temperature comprised between −10° C. and 15° C. In still another preferred embodiment, the addition of the coupling agent is performed at a temperature comprised between −10° C. and 25° C., preferably at the temperature of the interval of 20-25° C., and once the addition has ended, the reaction temperature is maintained. In another preferred embodiment, the coupling agent is DCI. Preferably, the reaction for forming the compound of formula (I-B) is carried out by means of stirring for approximately 1 to 3 days, more preferably for 1 to 2 days and still more preferably for approximately 24 hours. The reaction product can be purified by means of filtration and recrystallization. Solvents useful for recrystallizing the compound of formula (I-B) include $C_1$-$C_5$ alkanols ($C_nH_{2n+1}OH$), esters of $C_1$-$C_5$ carboxylic acids ($C_nH_{2n+1}$—COOH) with $C_1$-$C_5$ alkanols, $C_3$-$C_{11}$ ketones ($C_nH_{2n+1}$—CO—$C_nH_{2n+1}$) methyl-tert-butylether or toluene, preferably isopropanol and methyl-tert-butylether.

The present invention relates to a new method for synthesizing the compound of formula (D) through intermediates of formula (I-B) and (I-C), having a yield significantly greater than that achieved by means of the methods described in the state of the art. This will become evident throughout the present disclosure, particularly as a result of the examples. In turn, the compound of formula (D) thereby obtained can be used for synthesizing 3-[(4S)-8-bromo-1-methyl-6-(pyridin-2-yl)-4H-imidazo[1,2-a][1,4]benzodiazepin-4-yl]-propanoic acid methyl ester of formula (F).

Therefore, in a second aspect the invention relates to a method for preparing 3-[(4S)-8-bromo-1-methyl-6-(pyridin-2-yl)-4H-imidazo[1,2-a][1,4]benzodiazepin-4-yl]-propionic acid methyl ester of formula (F)

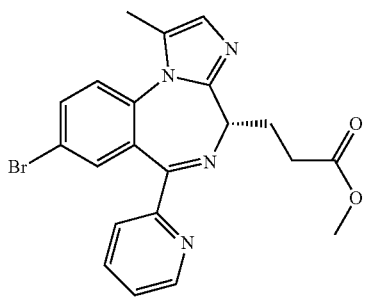

(F)

characterized in that it comprises the steps of:
a) reacting the compound of formula (D)

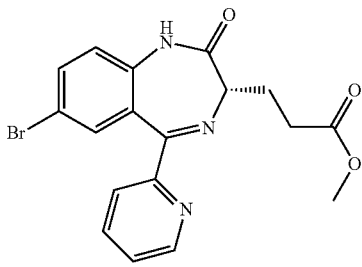

(D)

obtained by means of the method of the first aspect of the invention with lithium diisopropylamide (LDA) and bis-morpholinophosphorylchloride (BMPC) to obtain the compound of formula (E1)

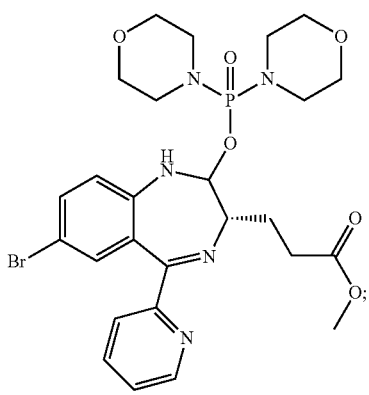

(E1)

b) reacting the compound of formula (E1) obtained in step (a) with (R)-1-amino-2-propanol or (S)-1-amino-2-propanol to obtain the compound of formula (EM)

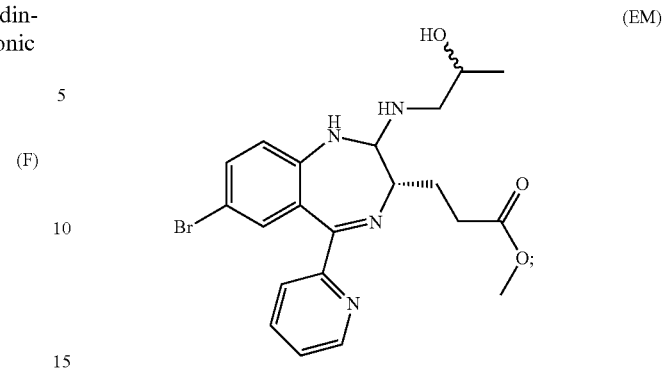

(EM)

and
c) reacting the compound of formula (EM) obtained in step (b) with the Dess-Martin periodinane oxidizing agent.

The Dess-Martin periodinane oxidizing agent is the compound with CAS number: 87413-09-0 the formula of which is shown below:

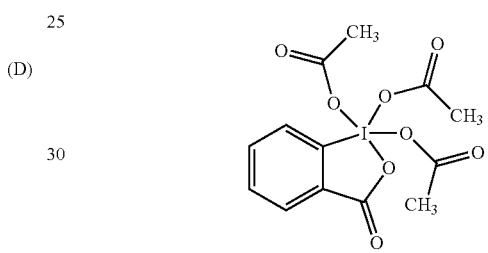

Steps (a), (b), and (c) have been described previously in application WO 2011/032692, but with the difference that in step (a) a compound of formula (D) obtained from a method different from the method object of the present invention is used.

Therefore, a particular embodiment of the present invention relates to the method for preparing a compound of formula (F) according to the method of the second aspect described above, characterized in that the compound of formula (D) is obtained from the compound of formula (I-C) according to the method of the first aspect of the invention.

In another particular embodiment, the present invention relates to a method for preparing a compound of formula (F) according to the method of the second aspect described above, characterized in that the compound of formula (D) is obtained from the compound of formula (I-C) according to the method of the first aspect of the invention, and in turn characterized in that the compound of formula (I-C) is obtained by reacting the compound of formula (I-B) with hydrobromic acid.

Another particular embodiment of the present invention relates to the method for preparing a compound of formula (F) according to the method of the second aspect described above, characterized in that the compound of formula (D) is obtained from the compound of formula (I-C) according to the method of the first aspect of the invention, characterized in that the compound of formula (I-C) is obtained by reacting the compound of formula (I-B) with hydrobromic acid, and in turn characterized in that the compound of formula (I-B) is obtained from the reaction of the compound of formula (A) with (2S)-2-(benzyloxycarbonylamino)-5-methoxy-5-oxo-pentanoic acid in the presence of a coupling agent.

The compounds of formula (I-C) and of formula (I-B) are described for the first time in the present disclosure. Said compounds are intermediates useful in the synthesis of the compound of formula (F). Therefore, a third aspect of the present invention relates to the use of methyl (4S)-4-amino-5-[4-bromo-2-(pyridin-2-carbonyl)anilino]-5-oxo-pentanoate hydrobromide salt of formula (I-C) for preparing a compound of formula (F). In a particular embodiment, said use is carried out by means of the method of the invention.

A fourth aspect of the present invention relates to the use of methyl (4S)-4-(benzyloxycarbonylamino)-5-[4-bromo-2-(pyridin-2-carbonyl)anilino]-5-oxo-pentanoate of formula (I-B) for preparing a compound of formula (F). In a particular embodiment, said use is carried out by means of the method of the invention.

As mentioned above, the compounds of formula (I-C) and of formula (I-B) are described for the first time in the present disclosure. Therefore, in a fifth aspect the present invention relates to the compound methyl (4S)-4-(benzyloxycarbonylamino)-5-[4-bromo-2-(pyridin-2-carbonyl)anilino]-5-oxo-pentanoate of formula (I-B)

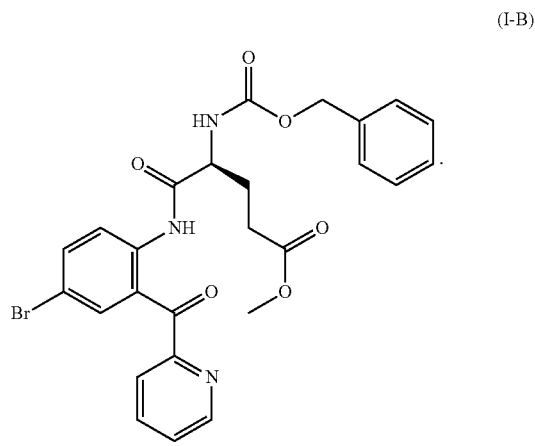 [SMILES: COC(=O)CC[C@H](NC(=O)OCc1ccccc1)C(=O)Nc1ccc(Br)cc1C(=O)c1ccccn1]

(I-B)

In a sixth aspect, the present invention relates to the compound methyl (4S)-4-amino-5-[4-bromo-2-(pyridin-2-carbonyl)anilino]-5-oxo-pentanoate hydrobromide salt of formula (I-C)

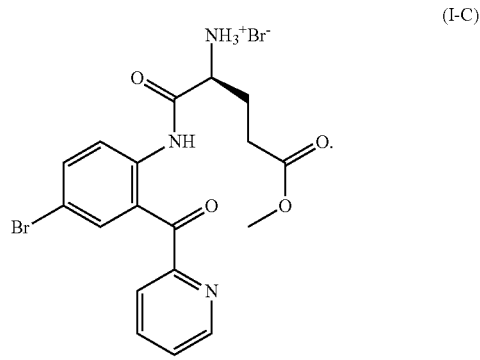

(I-C)

Example 1. Obtaining (2S)-2-(benzyloxycarbonylamino)-5-methoxy-5-oxo-pentanoic acid 22.4 g (139 mmol) of (2S)-2-amino-5-methoxy-5-oxo-pentanoic acid (Glu(OMe)-OH) were mixed with 420 ml of dichloromethane. The mixture was cooled at 0° C. and 30.2 g (278 mmol) of trimethylsilyl chloride were added, maintaining the temperature between 0 and 5° C. Next, 45.3 g (350 mmol) of N,N-diisopropylethylamine were slowly added, maintaining the temperature between 0 and 5° C. The resulting mixture was heated to reflux temperature and kept under stirring for 1 hour and 30 minutes. The reaction mixture was cooled at the temperature of 0° C. and 20 ml (23.9 g, 140 mmol) of benzyl chloroformate were added at a temperature between 0 and 5° C. The resulting reaction mixture was maintained at the indicated temperature for 30 minutes and then for 2 hours at a temperature of about 25° C.

The reaction mixture was vacuum-concentrated and 295 ml of an 8% aqueous sodium bicarbonate solution and 280 ml of isopropyl acetate were added. The aqueous phase was separated by means of decantation and acidified to a pH of about 2 by means of a 37% aqueous HCl solution. The aqueous phase resulting therefrom was extracted with isopropyl acetate (3×100 ml). The solvent of the pooled organic phases was distilled by means of vacuum until obtaining 40.7 g (99.0%) of a white solid with a purity greater than 99.0% corresponding to (2S)-2-(benzyloxycarbonylamino)-5-methoxy-5-oxo-pentanoic (Cbz-Glu(OMe)-OH) acid. The purity of the obtained products was analyzed by means of the ultra-high performance liquid chromatography technique in a Waters Acquity H-Class apparatus provided with a variable wave detector and a temperature-controlled oven for the column. FIG. 1 shows the 1H-NMR spectrum. 1H-NMR (CDCl$_3$, 400 MHz): 7.26 (5H, m), 5.47 (1H, d), 5.04 (2H, s), 4.37 (1H, m), 3.59 (3H, s), 2.3 (2H, m), 2.18 (1H, m) 1.96 (1H, m).

Example 2. Obtaining methyl (4S)-4-(benzyloxycarbonylamino)-5-[4-bromo-2-(pyridin-2-carbonyl)anilino]-5-oxo-pentanoate (I-B)

38.6 g (139 mmol) of (2-amino-5-bromophenyl)-pyridin-2-yl-methanone of formula (A) and 45.2 g (153 mmol) of (2S)-2-(benzyloxycarbonylamino)-5-methoxy-5-oxo-pentanoic acid were dissolved in 200 ml of dichloromethane at a temperature of about 15° C. The solution was cooled at −10° C. and a pre-prepared solution containing 32.2 g (156 mmol) of N,N'-dicyclohexylcarbodiimide in 65 ml of dichloromethane was slowly added at said temperature. The reaction mixture was kept under stirring at a temperature of about −10° C. for 48 hours, and the salts resulting from the reaction at a temperature of about 15° C. were then filtered.

Figure 2:
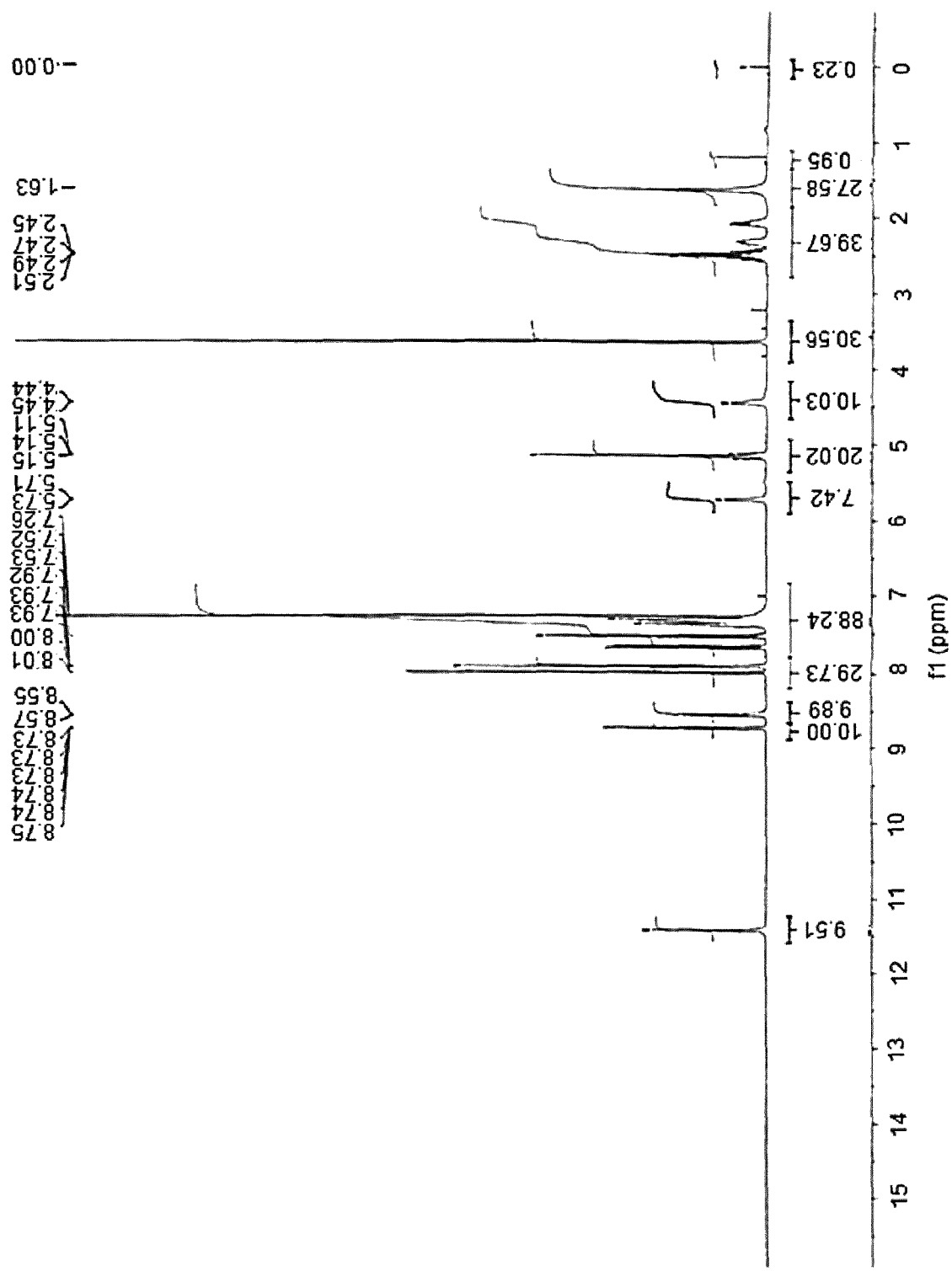
FIG. 2 shows the 1H-NMR of the compound of formula (I-B).

The reaction solvent was removed by means of vacuum distillation at a maximum temperature of 25° C. and 250 ml of methyl-tert-butylether were added. The obtained mixture was heated at 50° C. and then slowly cooled to a temperature of about 25° C. The resulting solid was filtered and dried in an oven at 50° C. 72.3 g (93.6%) of a slightly yellowish solid corresponding to methyl (4S)-4-(benzyloxycarbonylamino)-5-[4-bromo-2-(pyridin-2-carbonyl)anilino]-5-oxo-pentanoate of formula (I-B) were obtained in this manner. The purity of the obtained products was analyzed by means of the ultra-high performance liquid chromatography technique in a Waters Acquity H-Class apparatus provided with a variable wave detector and a temperature-controlled oven for the column. FIG. 2 shows the 1H-NMR spectrum. 1H-NMR (CDCl$_3$, 400 MHz): 11.43 (1H, s), 8.73 (1H, d), 8.56 (1H, d), 8 (1H, d), 7.93 (1H, s), 7.92 (1H, s), 7.67 (1H, dd), 7.52 (1H, m), 7.35 (5H, m), 5.71 (1H, d), 5.04 (2H, m), 4.45 (1H, m), 3.65 (3H, s), 2.50 (2H, m), 2.31 (1H, m), 2.07 (1H, m)

Example 3. Obtaining 3-[(3S)-7-bromo-2-oxo-5-(pyridin-2-yl)-2,3-dihydro-1H-[1,4]-benzodiazepin-3-yl] propionic acid methyl ester of formula (D)

35.0 g (63 mmol) of methyl (4S)-4-(benzyloxycarbonylamino)-5-[4-bromo-2-(pyridin-2-carbonyl)anilino]-5-oxo-pentanoate of formula (I-B) were dissolved in 70 ml of glacial acetic acid. Maintaining the temperature between 10 and 12° C., 45.7 ml (61.9 g, 253 mmol) of a 33 wt % pre-prepared solution of HBr in glacial acetic acid were slowly added. Once the addition ended, the temperature of the obtained mixture was left to increase to about 20° C. and it was kept under stirring for 2 hours between 15 and 20° C.

Figure 3:
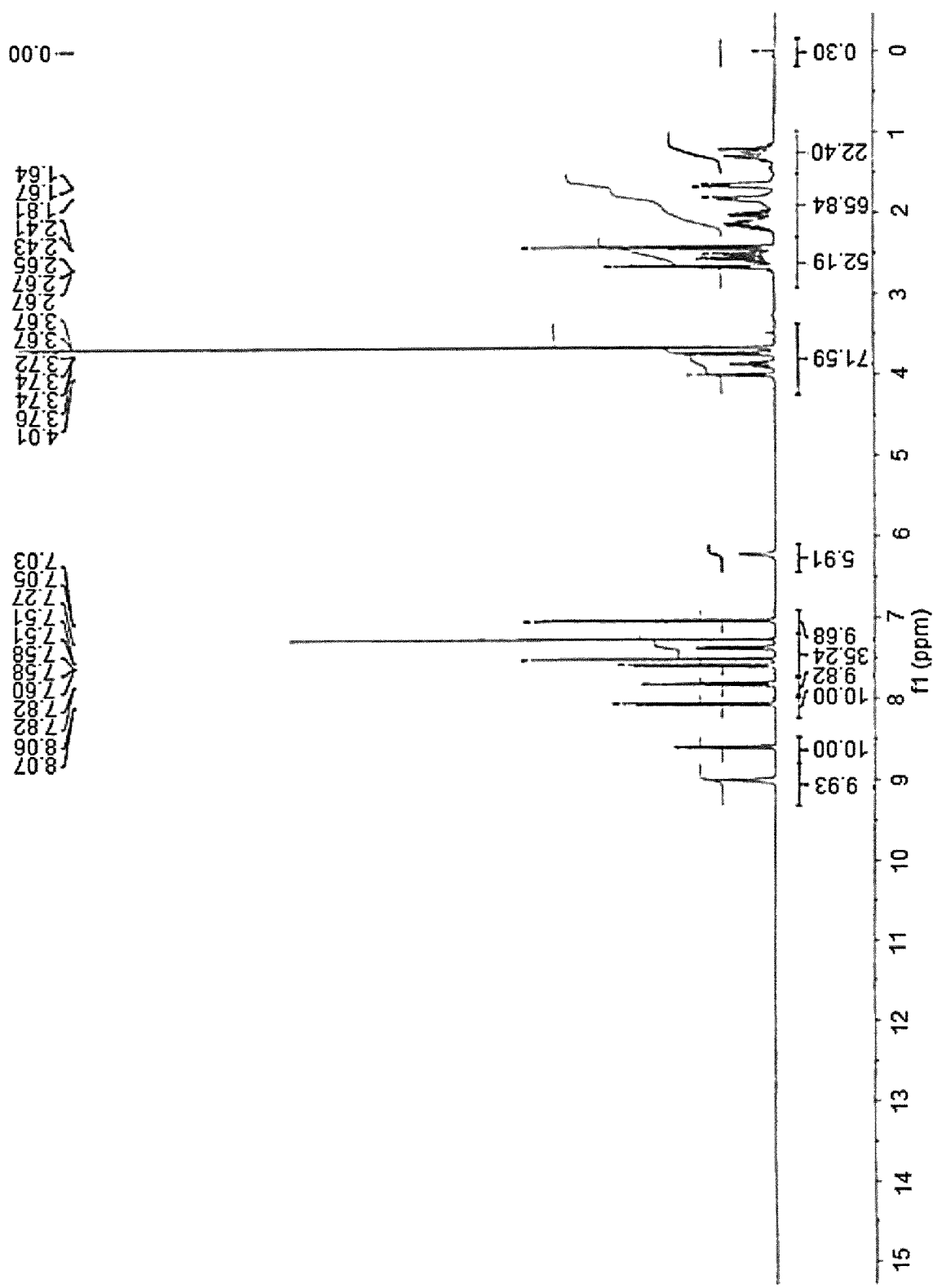
FIG. 3 shows the 1H-NMR of the compound of formula (D).

After being kept as described, 120 ml of water and 50 ml of dichloromethane were added. The resulting aqueous phase containing methyl (4S)-4-amino-5-[4-bromo-2-(pyridin-2-carbonyl)anilino]-5-oxo-pentanoate hydrobromide salt of formula (I-C) was separated, and the pH thereof was adjusted in the range of 3.8-4 by means of adding sodium bicarbonate at a temperature of about 25° C. Dichloromethane was added and the organic phase containing the reaction product corresponding to 3-[(3S)-7-bromo-2-oxo-5-(pyridin-2-carbonyl)-2,3-dihydro-1H-[1,4]-benzodiazepin-3-yl] propionic acid methyl ester of formula (D) was separated. The organic solvent was vacuum-distilled and 50 ml of isopropanol were added on the resulting residue. The obtained mixture was heated at reflux temperature (about 82° C.) and 50 ml of n-heptane were then added. The mixture was slowly cooled to about 20° C. and the resulting solid is filtered and dried in an oven, finally obtaining 22.4 g (88.2%) of 3-[(3S)-7-bromo-2-oxo-5-(pyridin-2-yl)-2,3-dihydro-1H-[1,4]-benzodiazepin-3-yl] propionic acid methyl ester of formula (D) with a purity of 99.0%. The purity of the obtained products was analyzed by means of the ultra-high performance liquid chromatography technique in a Waters Acquity H-Class apparatus provided with a variable wave detector and a temperature-controlled oven for the column. FIG. 3 shows the 1H-NMR spectrum. 1H-NMR (CDCl$_3$, 400 MHz): 9.01 (1H, s), 8.59 (1H, m), 8.05 (1H, d), 7.81 (1H, m), 7.58 (1H, m), 7.5 (1H, d), 7.36 (1H, m), 7.02 (1H, d), 3.74 (1H, m), 3.67 (3H, s), 2.67 (2H, m), 2.50 (2H, m).

Example 4. Obtaining methyl (4S)-4-amino-5-[4-bromo-2-(pyridin-2-carbonyl)anilino]-5-oxo-pentanoate hydrobromide salt of formula (I-C)

Figure 4:
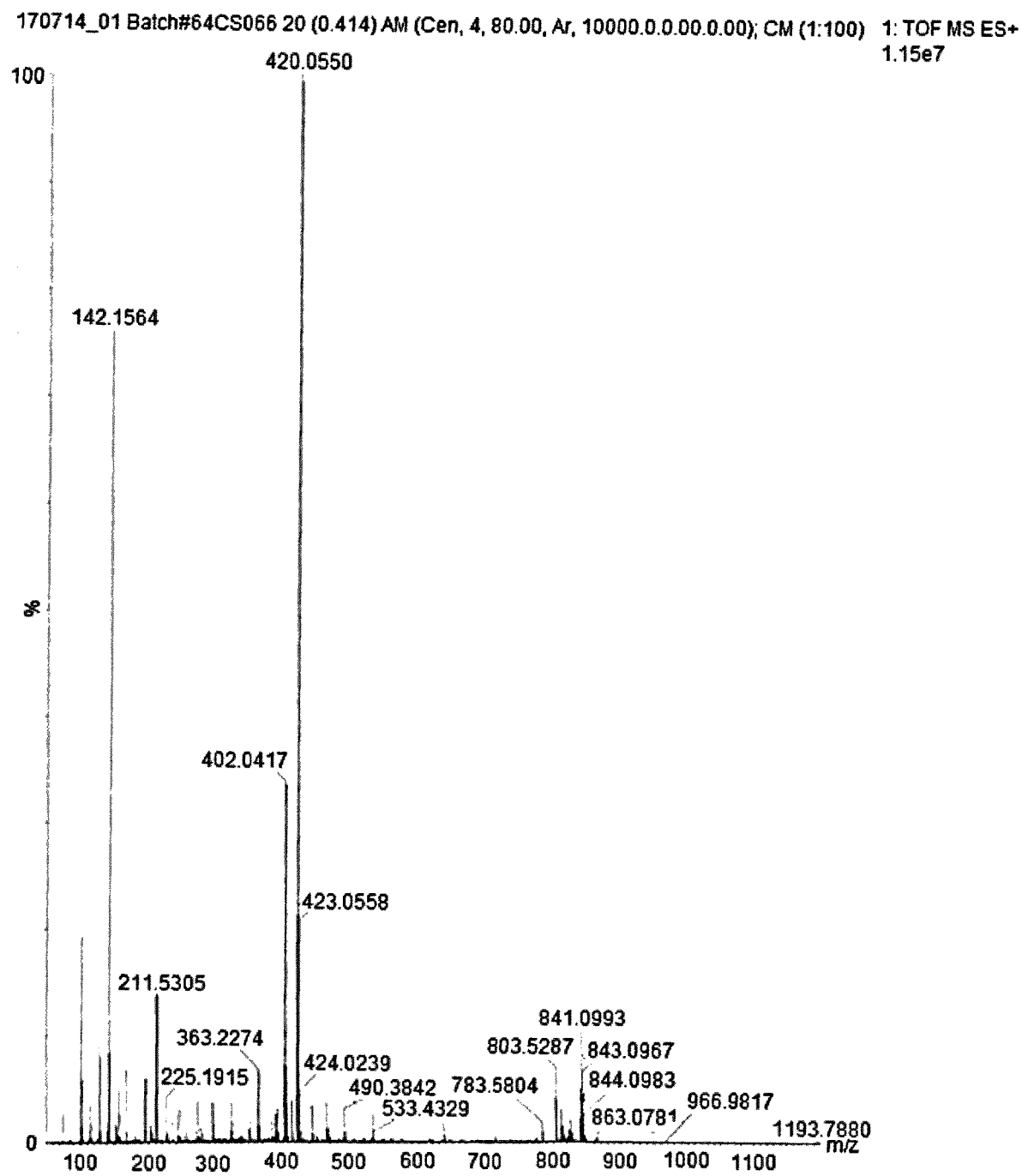
FIG. 4 shows the masses of the compound of formula (I-C).

35.0 g (63 mmol) of methyl (4S)-4-(benzyloxycarbonylamino)-5-[4-bromo-2-(pyridin-2-carbonyl)anilino]-5-oxo-pentanoate of formula (I-B) were dissolved in 70 ml of glacial acetic acid. Maintaining the temperature between 10 and 12° C., 45.7 ml (61.9 g, 253 mmol) of a 33 wt % pre-prepared solution of HBr in glacial acetic acid were slowly added. Once the addition ended, the temperature of the obtained mixture was left to increase to about 20° C. and it was kept under stirring for 2 hours between 15 and 20° C. A 4 ml aliquot of the crude reaction product was mixed at room temperature with 20 ml of isopropyl acetate, forming a solid which was isolated by means of filtration. The obtained solid was analyzed by means of the ultra-high performance liquid chromatography-mass spectrometry (UPLC-mass) technique in Waters Acquity UPLC equipment coupled to a Xevo G2 Tof YCA290 CL22ID detector. FIG. 4 shows that a monoisotopic mass value m/z of 420.0550 corresponding to molecular formula $C_{18}H_{19}N_3O_4Br$ was obtained for the signal with the higher percentage.

Example 5. Obtaining methyl (4S)-4-(benzyloxycarbonylamino)-5-[4-bromo-2-(pyridin-2-carbonyl)anilino]-5-oxo-pentanoate (I-B)

60.0 g (217 mmol) of (2-amino-5-bromophenyl)-pyridin-2-yl-methanone of formula (A) and 70.4 g (238 mmol) of (2S)-2-(benzyloxycarbonylamino)-5-methoxy-5-oxo-pentanoic acid were dissolved in 120 ml of dichloromethane at a temperature of about 20° C. 30.7 g (243 mmol) of N,N'-diisopropylcarbodiimide were slowly while maintaining the temperature within the interval of 20-25° C. After ending the addition the reaction mixture was kept under stirring within said temperature interval for 22 hours, and the salts resulting from the reaction were then filtered.

The reaction mixture obtained after filtration was washed with two 100 ml fractions of an aqueous 8% solution of NaHCO$_3$. The solvent was removed by means of vacuum distillation at a maximum temperature of 25° C. and 115 ml of isopropanol were added. The obtained mixture was heated at 70° C. and then 180 ml of methyl-tert-butyl ether were slowly added to the resulting solution. The resulting reaction mixture was cooled to a temperature of 0-5° C. and kept under stirring at said temperature during 2 hours. The resulting solid was filtered and dried in an oven at 50° C. 109.2 g (91.0%) of a practically non-colored solid corresponding to methyl (4S)-4-(benzyloxycarbonylamino)-5-[4-bromo-2-(pyridin-2-carbonyl)anilino]-5-oxo-pentanoate of formula (I-B) were obtained in this manner. The purity of the obtained products was analyzed by means of the ultra-high performance liquid chromatography technique in a Waters Acquity H-Class apparatus provided with a variable wave detector and a temperature-controlled oven for the column.

Comparative Example 1. Obtaining (2S)-2-(fluorophenylmethoxycarbonylamino)-5-methoxy-5-oxo-pentanoic acid 15.5 g (96 mmol) of (2S)-2-amino-5-methoxy-5-oxo-pentanoic acid (Glu(OMe)-OH) were mixed with 220 ml of dichloromethane. The mixture was cooled at 0° C. and 20.9 g (192 mmol) of trimethylsilyl chloride were added, maintaining the temperature between 0 and 5° C. Next, 25.0 g (193 mmol) of N,N-diisopropylethylamine were slowly added, maintaining the temperature between 0 and 5° C. The resulting mixture was heated to reflux temperature and kept under stirring for 1 hour and 30 minutes. The reaction mixture was cooled at a temperature of 0° C. and 24.9 ml (96 mmol) of fluorenylmethyl chloroformate were added at a temperature between 0 and 5° C. The resulting reaction mixture was maintained at the indicated temperature for 30 minutes and then at a temperature of about 20° C. for 1 hour and 30 minutes.

The reaction mixture was vacuum-concentrated and 160 ml of an 8% aqueous sodium bicarbonate solution and 160 ml of isopropyl acetate were added. The aqueous phase was separated by means of decantation and acidified to a pH of about 2 by means of a 37% aqueous HCl solution. The aqueous phase resulting therefrom was extracted with isopropyl acetate (3×100 ml). The solvent was distilled by means of vacuum until obtaining a residue which crystallized in isopropanol, yielding 35.0 g (94.9%) of a white solid with a purity of 99.1% corresponding to (2S)-2-(fluorophenylmethoxycarbonylamino)-5-methoxy-5-oxo-pentanoic acid (Fmoc-Glu(OMe)-OH). The purity of the obtained products was analyzed by means of the ultra-high performance liquid chromatography technique in a Waters Acquity H-Class apparatus provided with a variable wave detector and a temperature-controlled oven for the column.

Comparative Example 2. Obtaining (2S)-2-(fluorenyl-9-methoxycarbonylamino)-5-methoxy-5-oxo-pentanoic acid chloride 18.0 g (47 mmol) of (2S)-2-(fluorenyl-9-methoxycarbonylamino)-5-methoxy-5-oxo-pentanoic acid were dissolved in 126 ml of dichloromethane. The solution was cooled at a temperature of 20° C. and 0.25 ml of DMF and 6.7 g (56 mmol) of thionyl chloride were added. The resulting solution was kept under stirring at a temperature between 15 and 20° C. for 3 hours. The resulting mixture was then concentrated by means of vacuum to obtain, in a virtually quantitative manner, 19.5 g of a white solid corresponding to (2S)-2-(fluorenyl-9-methoxycarbonylamino)-5-methoxy-5-oxo-pentanoic acid chloride, which was used directly in the following reaction.

Comparative Example 3. Obtaining methyl (4S)-4-(fluorenyl-9-methoxycarbonylamino)-5-[4-bromo-2-(pyridin-2-carbonyl)anilino]-5-oxo-pentanoate of formula (B1)

19.5 g (47 mmol) of (2S)-2-(fluorenyl-9-methoxycarbonylamino)-5-methoxy-5-oxo-pentanoic acid chloride obtained in the preceding step were dissolved in 90 ml of dichloromethane and a pre-prepared solution of 13.0 g (47 mmol) of (2-amino-5-bromophenyl)-pyridin-2-yl-methanone of formula (A) in 40 ml of dichloromethane was added at a temperature between 0 and 10° C. The obtained mixture was kept under stirring at reflux temperature for 30 minutes.

Once the reaction ended, 100 ml of an 8% aqueous sodium bicarbonate solution and 100 ml of dichloromethane were added at a temperature of about 20° C. The organic phase was separated and concentrated by means of vacuum to obtain a residue to which 150 ml of isopropanol were added. The mixture was cooled at about 15° C. and the resulting solid was filtered to obtain 27.5 g (91.7%) of a solid corresponding to methyl (4S)-4-(fluorenyl-9-methoxycarbonylamino)-5-[4-bromo-2-(pyridin-2-carbonyl)anilino]-5-oxo-pentanoate. The purity of the obtained products was analyzed by means of the ultra-high performance liquid chromatography technique in a Waters Acquity H-Class apparatus provided with a variable wave detector and a temperature-controlled oven for the column.

Figure 5:
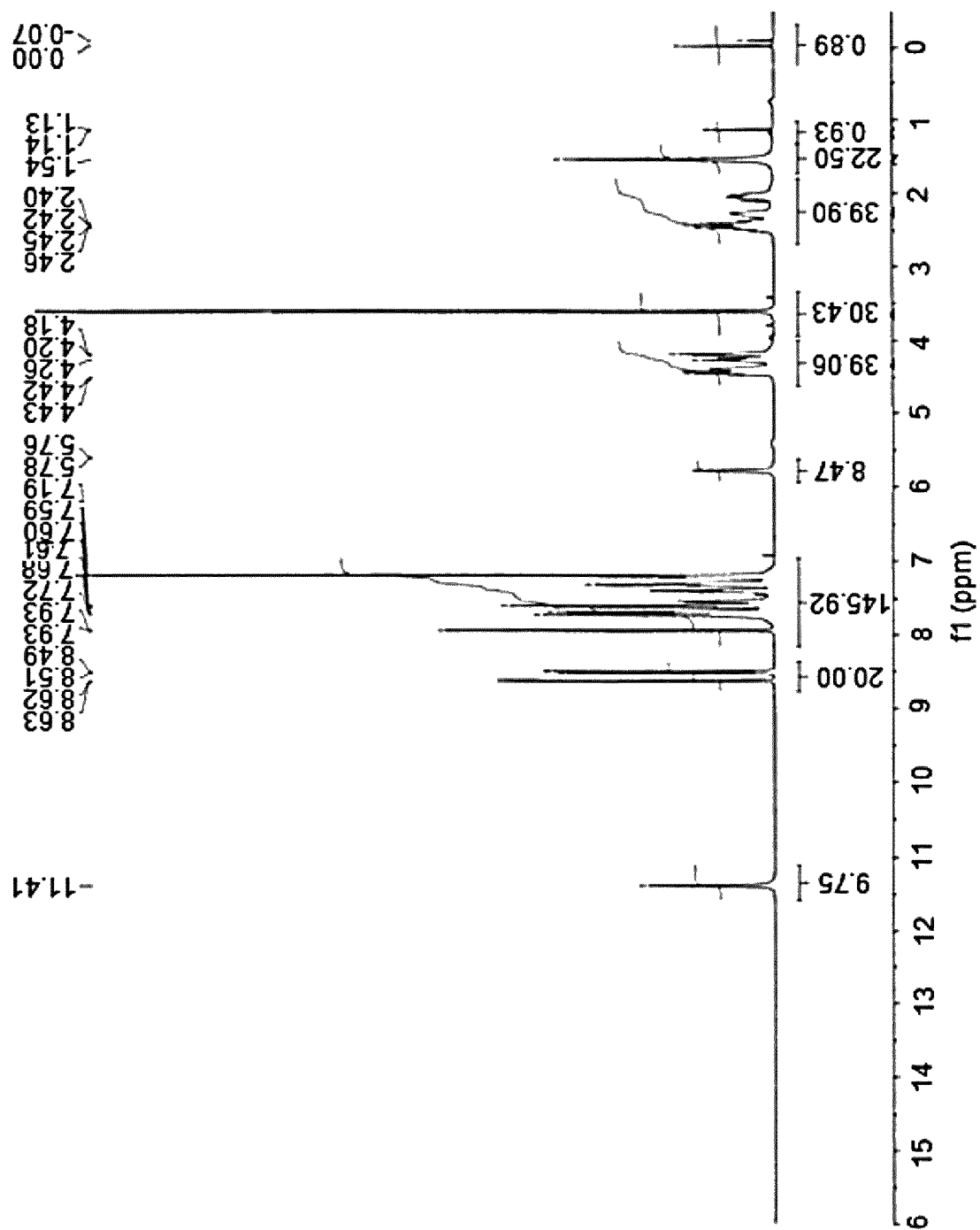
FIG. 5 shows the 1H-NMR of the compound of formula (B1).

FIG. 5 shows the 1H-NMR spectrum. 1H-NMR (CDCl$_3$, 400 MHz): 11.41 (1H, s), 8.62 (1H, m), 8.50 (1H, d), 7.93 (1H, d), 7.72 (2H, m), 7.68 (2H, m), 7.61 (1H, d), 7.59 (1H, d), 7.54 (1H, d), 7.40 (1H, m), 7.31 (1H, t), 7.21 (1H, t), 5.77 (1H, d), 4.41 (2H, m), 4.26 (1H, t), 4.18 (1H, t), 3.63 (3H, s), 2.43 (2H, m), 2.27 (1H, m), 2.04 (1H, m)

Comparative Example 4. Obtaining 3-[(3S)-7-bromo-2-oxo-5-(pyridin-2-yl)-2,3-dihydro-1H-[1,4]-benzodiazepin-3-yl] propionic acid methyl ester of formula (D) from methyl (4S)-4-(fluorenyl-9-methoxycarbonylamino)-5-[4-bromo-2-(pyridin-2-carbonyl)anilino]-5-oxo-pentanoate 16.8 g (26 mmol) of methyl (4S)-4-(fluorenyl-9-methoxycarbonylamino)-5-[4-bromo-2-(pyridin-2-carbonyl)anilino]-5-oxo-pentanoate were dissolved in 80 ml of dichloromethane and 48.8 g (482 mmol) of triethylamine were added. Once the addition ended, the obtained mixture was kept under stirring overnight at a temperature between 40 and 45° C.

After being kept as described, the reaction mixture was concentrated by means of vacuum to obtain a residue to which 40 ml of acetone were added. It was heated at reflux, obtaining a homogeneous mixture which was cooled at a temperature of about 20° C. The resulting solid was filtered and washed with acetone, yielding a product containing 62% of 3-[(3S)-7-bromo-2-oxo-5-(pyridin-2-yl)-2,3-dihydro-1H-[1,4]-benzodiazepin-3-yl] propionic acid methyl ester of formula (D). This solid was recrystallized in isopropanol, obtaining 4.2 g (40%) of the desired product with a purity of 94%. The purity of the obtained products was analyzed by means of the ultra-high performance liquid chromatography technique in a Waters Acquity H-Class apparatus provided with a variable wave detector and a temperature-controlled oven for the column.

What is claimed is:

1. A method for preparing 3-[(3S)-7-bromo-2-oxo-5-(pyridin-2-yl)-2,3-dihydro-1H-[1,4]-benzodiazepin-3-yl] propionic acid methyl ester of formula (D)

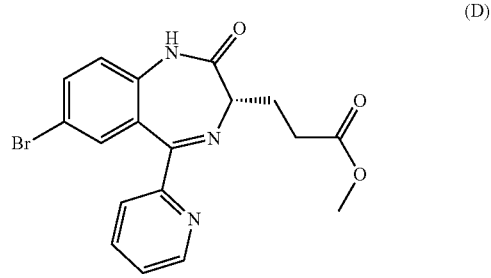 [SMILES: COC(=O)CC[C@@H]1N=C(c2ccccn2)c2cc(Br)ccc2NC1=O]

(D)

comprising reacting methyl (4S)-4-amino-5-[4-bromo-2-(pyridin-2-carbonyl)anilino]-5-oxo-pentanoate hydrobromide salt of formula (I-C)

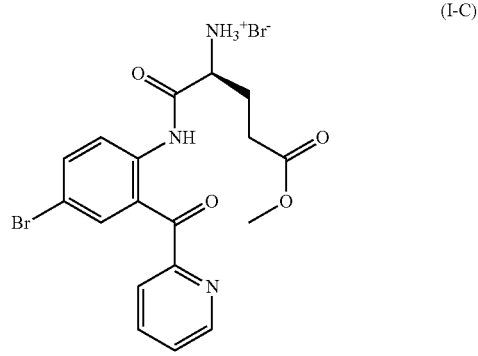

(I-C)

with a base, wherein the compound of formula (I-C) is prepared by means of reacting methyl (4S)-4-(benzyloxycarbonylamino)-5-[4-bromo-2-(pyridin-2-carbonyl)anilino]-5-oxo-pentanoate (I-B)

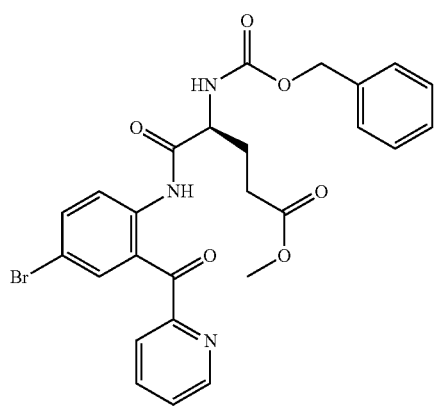

with hydrobromic acid.

2. The method according to claim 1, wherein the methyl (4S)-4-(benzyloxycarbonylamino)-5-[4-bromo-2-(pyridin-2-carbonyl)anilino]-5-oxo-pentanoate of formula (I-B) is prepared by means of reacting the compound of formula (A)

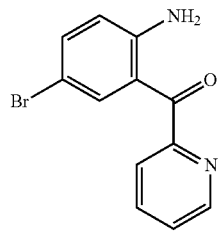

with (2S)-2-(benzyloxycarbonylamino)-5-methoxy-5-oxo-pentanoic acid in the presence of a coupling agent.

3. A method for preparing 3-[(4S)-8-bromo-1-methyl-6-(pyridin-2-yl)-4H-imidazo[1,2-a][1,4]benzodiazepin-4-yl]-propionic acid methyl ester of formula (F),

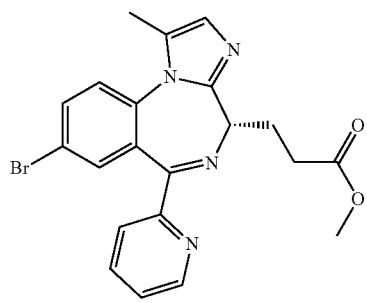

comprising:
a) preparing the compound of formula (D) according to the method of claim 1

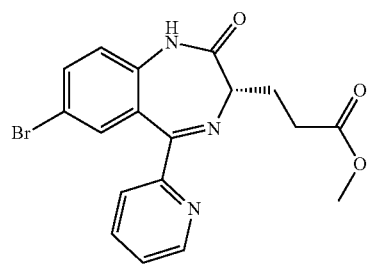

b) reacting the compound of formula (D) with lithium diisopropylamide (LDA) and bis-morpholinophosphorylchloride (BMPC) to obtain the compound of formula (E1)

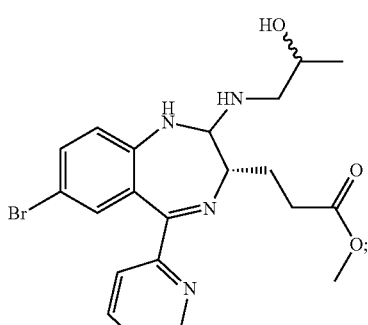

c) reacting the compound of formula (E1) obtained in said (b) with (R)-1-amino-2-propanol or (S)-1-amino-2-propanol to obtain the compound of formula (EM)

(EM)

and
d) reacting the compound of formula (EM) obtained in said (c) with the Dess-Martin periodinane oxidizing agent.

4. The method for preparing a compound of formula (F) according to claim 3, wherein the compound of formula (I-B) is obtained by reacting the compound of formula (A)

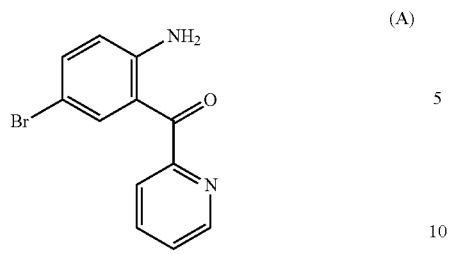
(A)
with (2S)-2-(benzyloxycarbonylamino)-5-methoxy-5-oxo-pentanoic acid in the presence of a coupling agent.
5. Methyl (4S)-4-(benzyloxycarbonylamino)-5-[4-bromo-2-(pyridin-2-carbonyl)anilino]-5-oxo-pentanoate of formula (I-B)
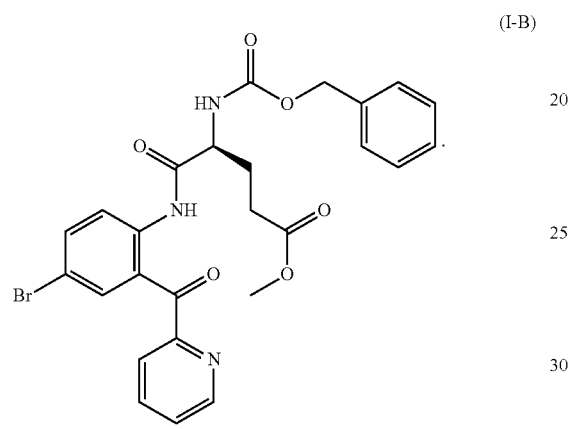
(I-B)
* * * * *